United States Patent [19]
Takemoto et al.

[11] Patent Number: 5,466,864
[45] Date of Patent: Nov. 14, 1995

[54] METHOD FOR RECOVERING L-PHENYLALANINE

[75] Inventors: Tadashi Takemoto; Toyoto Hijiya; Teruo Yonekawa; Chiaki Mochizuki, all of Kawasaki, Japan

[73] Assignee: Ajinomoto Co., Inc., Tokyo, Japan

[21] Appl. No.: 190,450

[22] Filed: Feb. 2, 1994

[30] Foreign Application Priority Data

Feb. 25, 1993 [JP] Japan ................................ 5-036880
Feb. 25, 1993 [JP] Japan ................................ 5-036881
Mar. 22, 1993 [JP] Japan ................................ 5-061972

[51] Int. Cl.⁶ ............................................. C07C 53/134
[52] U.S. Cl. ................................................ 562/445; 558/43
[58] Field of Search ................................. 558/43; 562/445

[56] References Cited

U.S. PATENT DOCUMENTS

4,399,304  8/1983  Matsuishi et al. .

FOREIGN PATENT DOCUMENTS

0055612  7/1982  European Pat. Off. .

*Primary Examiner*—Nicky Chan
*Attorney, Agent, or Firm*—Oblon, Spivak, McClelland, Maier, & Neustadt

[57] ABSTRACT

The present invention provides crystals of L-phenylalanine monomethyl sulfate which have low solubility compared to L-tyrosine and D-phenylalanine. The L-phenylalanine monomethylsulfate crystals are obtained by subjecting a solution containing monomethyl sulfuric acid and phenylalanine to crystallization.

Further, the present invention also provides a process for recovering L-phenylalanine from a water layer by neutralizing the esterified reaction, extracting an ester of L-phenylalanine therefrom with an organic solvent, and recovering remaining L-phenylalanine in the water layer as L-phenylalanine monomethylsulfate. L-phenylalanine monomethyl sulfate is obtained by esterifying L-phenylalanine and methanol in the presence of sulfuric acid, neutralizing the esterified solution with a base in the presence of water, extracting the produced L-phenylalanine methyl ester from the neutralized solution with an organic solvent, and then crystallized the resultant water layer under acidic condition.

8 Claims, 3 Drawing Sheets

METHOD FOR RECOVERING L-PHENYLALANINE

BACKGROUND OF THE INVENTION

1. Field of the Invention

L-phenylalanine and its methyl ester, L-phenylalanine methyl ester are useful intermediates in peptide synthesis. The demand for these compounds in recent years has increased because they are also starting materials in the synthesis of α-L-aspartyl-L-phenylalanine methyl ester, a popular sweetener. This invention relates to a novel process for recovering L-phenylalanine from syntheses by formation of an optically active L-phenylalanine monomethylsulfate crystal.

2. Discussion of Background

For convenience, the abbreviations used hereinafter are summarized in the following Table:

| Compound | Abbreviation |
| --- | --- |
| L-aspartyl-L-phenylalanine methyl ester | L-L-APM |
| α-aspartyl-phenylalanine methyl ester | α-APM |
| α-L-aspartyl-L-phenylalanine methyl ester | α-L-L-APM |
| L-aspartic acid | L-Asp |
| L-phenylalanine | L-Phe |
| D-phenylalanine | D-Phe |
| DL-phenylalanine | DL-Phe |
| L-tyrosine | L-Tyr |
| L-phenylalanine methyl ester | L-PM |
| L-phenylalanine monomethyl sulfate | $L\text{-Phe}\cdot CH_3SO_4H$ |

Conventional L-phenylalanine syntheses produce product whose quality is low due to the presence of two impurities. For example, when L-Phe is prepared by a fermentation, it is usually contaminated with L-Tyr, also present in the fermentation broth, and with D-Phe, an optical isomer of L-Phe.

It is known that L-Phe can be selectively crystallized from L-Tyr by derivatizing the carboxy or amino terminus of L-Phe (for example with L-phenylalanine 1 sodium 5 hydrate as disclosed in Japanese Patent Laid Open No. 60-13746 or L-phenylalanine ½ sulfate ½ hydrate as disclosed in Japanese Patent Laid Open No. 56-79652). However, the solubility of crystals of these L-Phe derivatives increases during crystallization resulting in losses of product into the mother liquor and thus decreased yields. In order to achieve higher yields, crystallization must be performed at high concentrations of L-Phe. As a result, the force necessary to stir the aqueous slurry increases. Additionally, impurities in the mother liquor can adhere to the isolated crystals.

D-Phe is produced as a result of racemization of L-Phe under the high-temperature and alkali conditions used to treat the fermentation broth. D-Phe is also produced as a result of racemization during manufacturing processes which use L-Phe or L-Phe derivatives as starting materials. D-Phe is also produced during attempts to recover L-Phe from these processes (L-Phe is frequently recovered by removing any derivatizing groups by suitable methods such as hydrolysis).

Unfortunately, D-Phe produced during the manufacture of L-Phe is difficult to separate from L-Phe under common crystallization conditions, because D-Phe forms a pair with L-Phe to form a DL-Phe crystal. Since the solubility of DL-Phe is generally far lower than that of the L-Phe, it is difficult to isolate L-Phe.

Various methods have also been studied for recovering L-Phe from manufacturing processes which prepare α-APM. During the production of α-APM, L-Phe is methyl-esterified and the resultant L-PM is condensed with L-Asp whose amino group is protected to produce N-protected-α-L-L-APM. Thereafter, the protecting group is removed yielding α-L-L-APM.

To obtain L-PM, L-Phe is esterified with methanol in the presence of an acid such as hydrochloric acid or sulfuric acid; the resultant acidic reaction solution is then neutralized with a suitable base in the presence of water; and subsequently L-PM is extracted with a water-immiscible organic solvent such as toluene. In this method, any L-Phe which is not esterified and L-Phe which is produced as a result of the decomposition of L-PM during the neutralization and extraction steps dissolve into the extracted water layer. In addition, any L-PM not extracted into the organic solvent is also dissolved therein.

Since L-Phe is a relatively expensive starting material, it is desirable to recover it from industrial processes and reuse it as a starting material. For example, in the process of preparing α-APM, L-Phe is recovered from the mother liquor after α-APM has been crystallized (Japanese Patent Laid Open No. 63-159355; Japanese Patent Laid Open No. 57-130958 etc.). However, no economic or simple method has yet been found to recover the dissolved L-Phe from the above mentioned extracted water layer.

L-Phe is dissolved in low concentration and thus the extracted water layer has to be concentrated before L-Phe can be recovered by crystallization. Since a large amount of energy is required to concentrate the extracted layer, the recovery of L-Phe becomes economically unfeasible.

SUMMARY OF THE INVENTION

Figure 1:
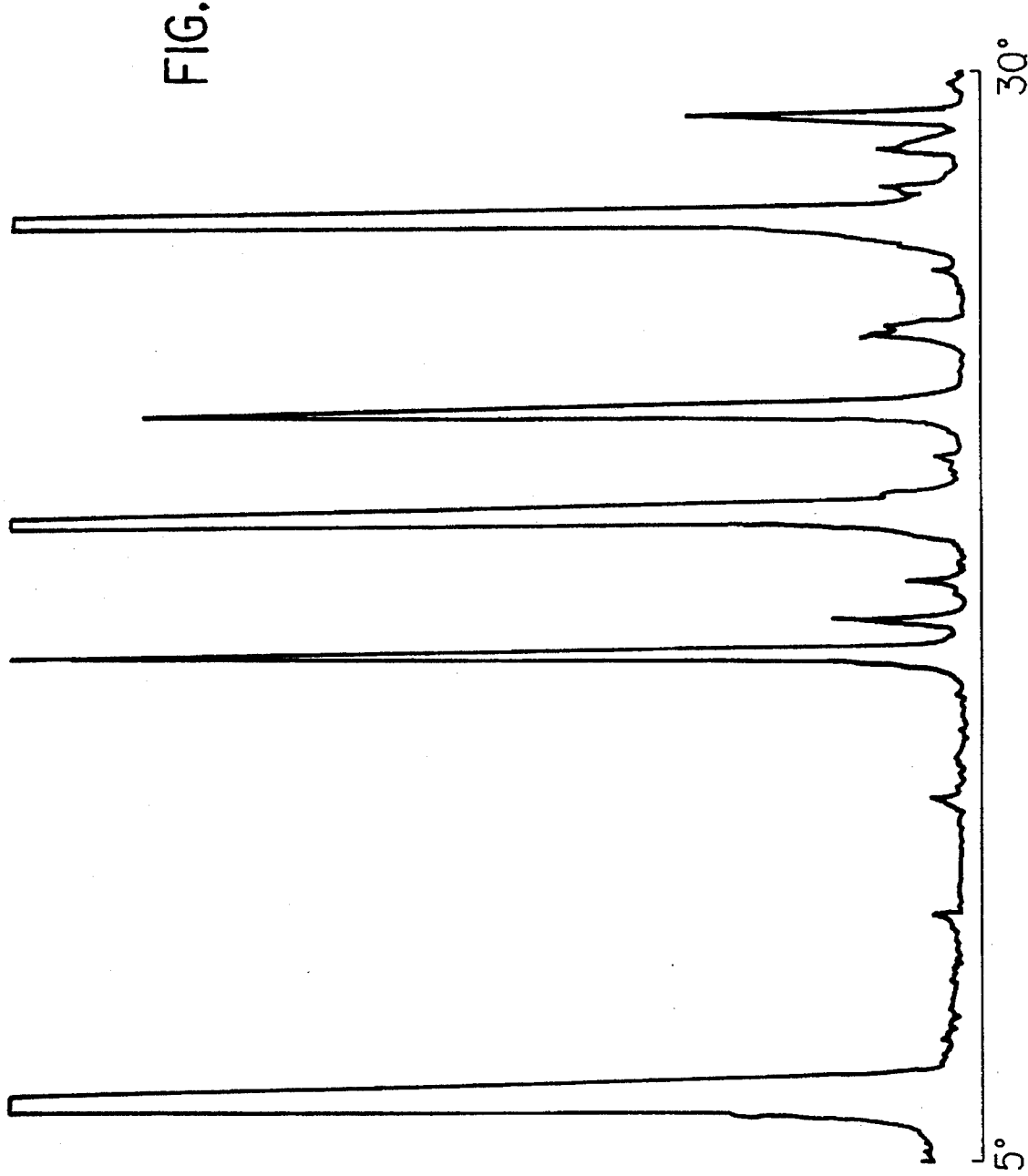
FIG. 1. An X-ray powder diffraction pattern of a crystal obtained according to Example 1 ($CuK_\alpha$ ray).

Accordingly, one object of the present invention is to find a L-Phe salt which can be readily obtained and can be separated selectively from solvent containing impurities such as L-Tyr and D-Phe.

A second object of the present invention is to find a method of recovering L-Phe from manufacturing processes where it is used as a starting material. In particular, the present invention seeks to provide a method of recovering L-Phe from the water layer obtained after neutralizing a solution of L-PM and methyl-esterified L-Phe and extracting L-PM therefrom with an organic solvent.

The present inventor have now surprisingly found that a L-phenylalanine monomethylsulfate crystal of high purity can be obtained by crystallizing an aqueous solution which has low optical purity and contains both L-Phe and a $CH_3SO_4H$ salt. $L\text{-Phe}\cdot CH_3SO_4H$ selectively crystallizes compared to L-Tyr, D-Phe and other impurities.

In addition, pure $L\text{-Phe}\cdot CH_3SO_4H$ crystals can be obtained by crystallizing a solution containing racemic DL-Phe and $CH_3SO_4H$. These crystal have the same X-ray powder spectrum and infrared spectrum as crystals obtained from L-Phe. This is an important as it provides an effective method for optically purifying an optically impure L-Phe.

Further, it has been surprisingly revealed that L-Phe.$CH_3SO_4H$ crystals can be readily obtained by esterifying L-Phe and methanol in the presence of sulfuric acid; neutralizing the resultant acidic reaction solution with a suitable base; extracting the produced L-PM with toluene; acidifying the water layer and crystallizing L-Phe with at least a stoichiometric amount of $CH_3SO_4H$. By redissolving the obtained crystals in water and neutralizing with base, L-Phe crystals can be obtained.

DETAILED DESCRIPTION OF THE PREFERRED EMBODIMENTS

The amount of $CH_3SO_4H$ used to crystallize L-Phe out of solution in the present invention may be equimolar or 100 times (molar ratio) the corresponding amount of L-Phe. If the amount of $CH_3SO_4H$ is lower than equimolar, crystallization yields are reduced. Further, when $CH_3SO_4H$ is equimolar or less than L-Phe, L-Phe crystals as well as L-Phe.$CH_3SO_4H$ crystals may be produced. In such a case, free L-Phe can be obtained readily from the mixed crystals in a manner described below. As the amount of $CH_3SO_4H$ increases, the solubility of the resulting crystals drastically decreases and the crystallization yields are increased. However, adding an unnecessarily large amount of $CH_3SO_4H$ is not economical.

$CH_3SO_4H$ can be prepared readily with methanol and sulfuric acid. Alternatively, it is possible to obtain $CH_3SO_4H$ from a solution of a salt of $CH_3SO_4H$ by converting the salt into a free acid with an acid such as sulfuric acid or hydrochloric acid. Suitable $CH_3SO_4H$ salts which can be so converted include alkali metal salts such as sodium and potassium; alkali earth metals such as calcium; and amine salts such as ammonia and triethylamine.

In the present invention, it is preferable to crystallize L-Phe.$CH_3SO_4H$ in an aqueous solvent, however organic solvents may also be present. Organic solvents such as alcohols such as methanol and ethanol; ketones such as acetone; carboxylic acids such as formic acid and acetic acid; and nitriles such as acetonitrile can be present.

Crystallization can be achieved by conventional methods such as concentrating crystallization and cooling crystallization. Cooling crystallization is preferred because the solubility can be controlled by adjusting the temperature. Alternatively, it is possible to obtain L-Phe.$CH_3SO_4H$ by mixing an aqueous solution containing L-Phe and $CH_3SO_4H$ with a water-miscible organic solvent. The solubility of the L-Phe.$CH_3SO_4H$ salt is generally lower in organic solvents than it is in water. In addition, neutralizing crystallization with acid can also be used when $CH_3SO_4H$ is a basic salt.

In order to obtain L-Phe.$CH_3SO_4H$ crystals, it is sufficient that $CH_3SO_4H$ and L-Phe are present in the crystallization system; that is, crystallization is not affected by the order in which they are mixed. For example, if sodium monomethylsulfate is first neutralized with sulfuric acid, and L-Phe in a crystalline state is subsequently added or if L-Phe is dissolved in a sulfuric acid solution, and either $CH_3SO_4H$ or sodium monomethylsulfate is then added, L-Phe.$CH_3SO_4H$ crystals will still be produced.

The solubility of L-Phe.$CH_3SO_4H$ is greatly affected by the amount of corresponding $CH_3SO_4H$ and the type and contents of the solvent. When an organic solvent is present, the concentration of L-Phe should be equal to or larger than 0.1 g/dl. When substantially no organic solvent is present, the crystallization is preferably carried out at concentrations of L-Phe equal to or larger than 1 g/dl.

The solubility of L-Phe.$CH_3SO_4H$ becomes low and the crystallization yields increase when crystallization is carried out at low temperatures. Preferably, the temperature during crystallization is kept not higher than 60° C. and preferably not higher than 30° C.

The L-Phe.$CH_3SO_4H$ salt obtained in the manner described above can readily form free L-Phe by means of, for example, removing $CH_3SO_4H$ from the solution thereof using an anion ion exchange resin or neutralizing the solution with a suitable base such as sodium hydroxide, potassium hydroxide, sodium carbonate, sodium hydrogen carbonate or ammonia. The free L-Phe can then be crystallized.

While above mentioned description has been made in conjunction with the L-Phe.$CH_3SO_4H$ salt, it is apparent that this method is equally applicable to the antipode, D-Phe.$CH_3SO_4H$ salt. The solubility of L-Phe.$CH_3SO_4H$ is the same as that of D-Phe.$CH_3SO_4H$. Therefore, when L-Phe.$CH_3SO_4H$ exists in a little excess amount compared with D-Phe.$CH_3SO_4H$, L-Phe can be separated as crystals of L-Phe.$CH_3SO_4H$ by adding a solvent in an amount which is enough to dissolve D-Phe.$CH_3SO_4H$ (i.e., the same amount of L-Phe.$CH_3SO_4H$ is dissolved in the solvent). On the other side, if an excess amount of D-Phe.$CH_3SO_4H$ exists, D-Phe can be separated as crystals of D-Phe.$CH_3SO_4H$. Either L-Phe or D-Phe which exists in an excess amount always can be separated as its $CH_3SO_4H$ salt.

When L-Phe.$CH_3SO_4H$ is formed from the water layer obtained by esterifying L-Phe and methanol in the presence of sulfuric acid; neutralizing the resultant acidic reaction with a base; extracting the produced PM with an organic solvent, the following reaction conditions are preferred.

To neutralize the esterified reaction solution, any typical bases can be used including sodium carbonate, sodium bicarbonate, sodium hydroxide, potassium hydroxide and ammonia. The concentration of these bases is not particularly limited, but a 5–50% solution is commonly used.

The organic solvent used for extraction is not specifically limited as long as it is water-immiscible. Suitable solvents include aromatic hydrocarbons such as toluene and benzene, carboxylates such as ethyl acetate and ethyl formate, ethers such as ethyl ether and isopropyl ether, and halogenated hydrocarbons such as chloroform and methylene chloride.

The water layer used to extract L-PM may contain the organic solvent and methanol dissolved therein as neither seriously affects the crystallization. Especially since when the crystallization is conducted under concentrated conditions, any organic solvent having a low boiling points or which azeotropes with water is removed during the concentration operation prior to the crystallization.

The extracted water is concentrated under acidic condition up to the concentration that is sufficient to precipitate L-Phe.$CH_3SO_4H$ salt. Alternatively, the aqueous layer may be concentrated before it is adjusted with acid. However, monomethyl sulfuric acid is more likely to be decomposed under alkali conditions as compared to acidic conditions, so that the former treatment procedure is preferred.

The degree to which the aqueous layer is concentrated depends on the amount of L-Phe dissolved therein. To give an example, L-Phe.$CH_3SO_4H$ can be separated from the water layer obtained by neutralizing with 15% $Na_2CO_3$ solution and extracting a 95% esterified solution of L-PM when the water layer is concentrated into ½ to ⅓. On the contrary, if the same water layer containing L-Phe is crystallized at the isoelectric point, it should be concentrated into 1/10 or less to recover L-Phe economically.

As an acid for adjusting the extracted water layer into acidic condition, any acid can be used. Preferably inexpensive acids such as mineral acid like hydrochloric acid, sulfuric acid and phosphoric acid, methane sulfonic acid and monomethyl sulfuric acid are used.

The pH of the extracted water layer is adjusted to a pH of not larger than 3. Preferably, the pH is adjusted to a pH of not larger than 2, and more preferably to a pH of not larger than 1.

The crystallization technique is not limited and may be the cooling crystallization or the concentrated crystallization. However, the solubility of the L-Phe.$CH_3SO_4H$ salt varies greatly depending on the temperature and the solubility is more degraded at the lower temperature. Accordingly, it is preferable to crystallize at a low temperature in the viewpoint of crystallization yields. The temperature may be not larger than 60° C., preferably not larger than 30° C., and more preferably not larger than 15° C.

The crystal obtained through crystallization in the acidic condition is L-Phe.$CH_3SO_4H$ salt, so that monomethyl sulfuric acid of equivalent amount may be enough with respect to L-Phe. However, excess amount of monomethyl sulfuric acid results in lower solubility of L-Phe.$CH_3SO_4H$ salt because of the salting-out effect to increase the crystallization yields. Twice the equivalent amount or more is preferable.

However, for the above mentioned extracted water layer produced from the esterified reaction solution of esterification reacted rate of 95% or more, twenty times of the equivalent amount or more monomethyl sulfuric acid component is present with respect to L-Phe.

Such system may be crystallized as it is, but a large amount of monomethyl sulfuric acid adheres to the isolated crystals. The monomethyl sulfuric acid is highly soluble to water and thus can be removed readily with water. In such a case, it is possible to crystallize by adding L-Phe into the extracted water layer to reduce the proportion of monomethyl sulfuric acid to equal to or slightly more than one molar equivalent. In this way, crystallization can be made without concentrating the extracted water layer. In addition, if D,L-Phe is added to reduce the proportion of $CH_3SO_4H$, the resultant crystals have high optical purity; that is D-Phe.$CH_3SO_4H$ does not crystallize as well as L-Phe.$CH_3SO_4H$.

Needless to say, this optical purification is also obtained if the L-Phe used for esterification contains D-Phe as an impurity.

L-Phe.$CH_3SO_4H$ salt obtained in the manner described above can readily form free L-Phe by means of, for example, removing $CH_3SO_4H$ from the solution thereof using an anion ion exchange resin or neutralizing the solution with a suitable base as described above.

Having generally described this invention, a further understanding can be obtained by reference to certain specific examples which are provided herein for purposes of illustration only and are not intended to be limiting unless otherwise specified.

EXAMPLES

EXAMPLE 1

13.4 g (0.1 mol) $CH_3SO_4Na$ and 4.13 g (25 mmol) L-Phe were added to 35 mL of water and adjusted with sulfuric acid to pH 0. The mixture was heat-dissolved at about 70° C. and then cooled. The separated crystals were isolated by a suction filtration, washed with a small amount of water and dried under reduced pressure.

Figure 2:
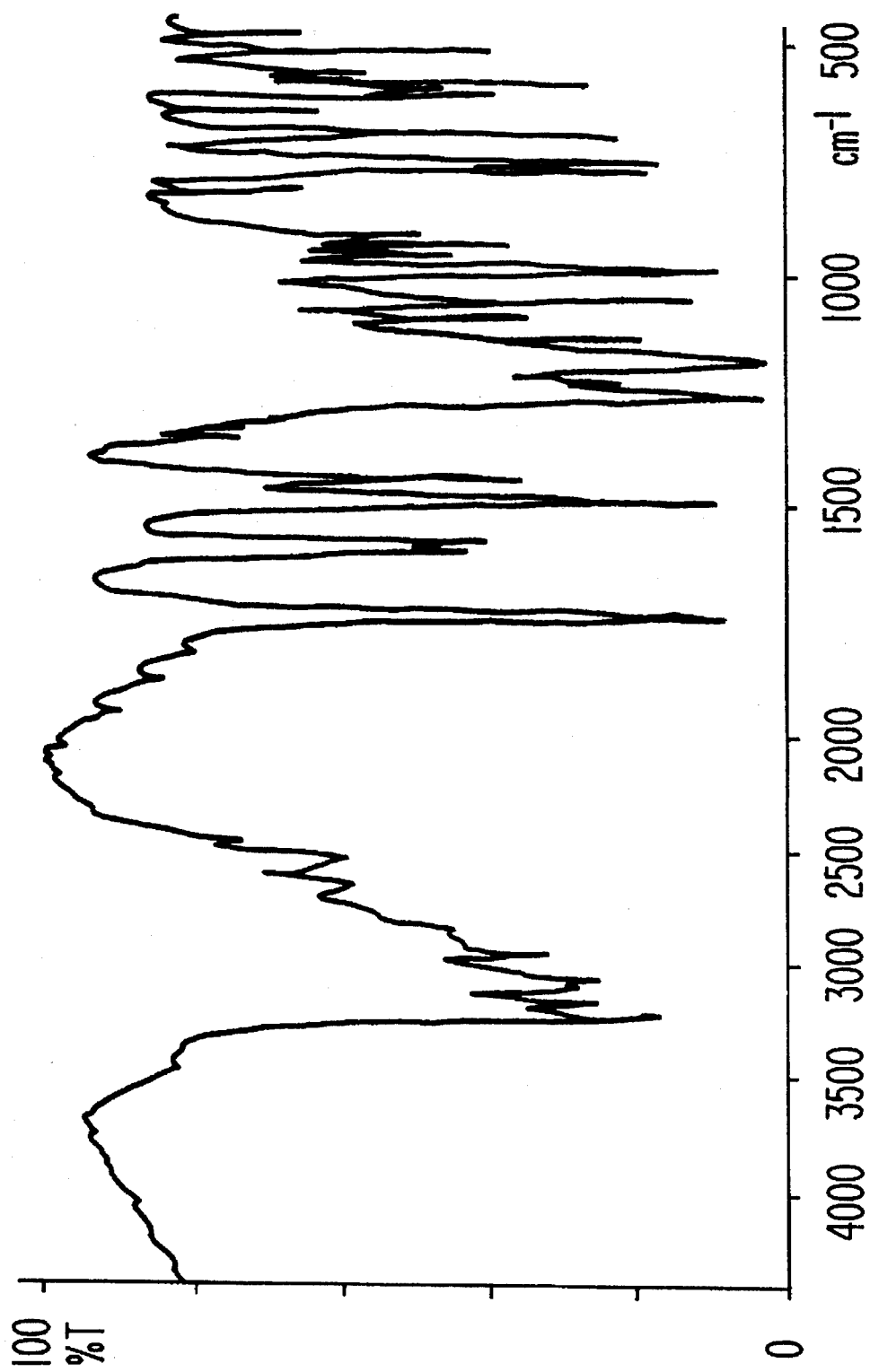
FIG. 2. An IR chart of a crystal obtained according to Example 1 (KBr method).
Figure 3:
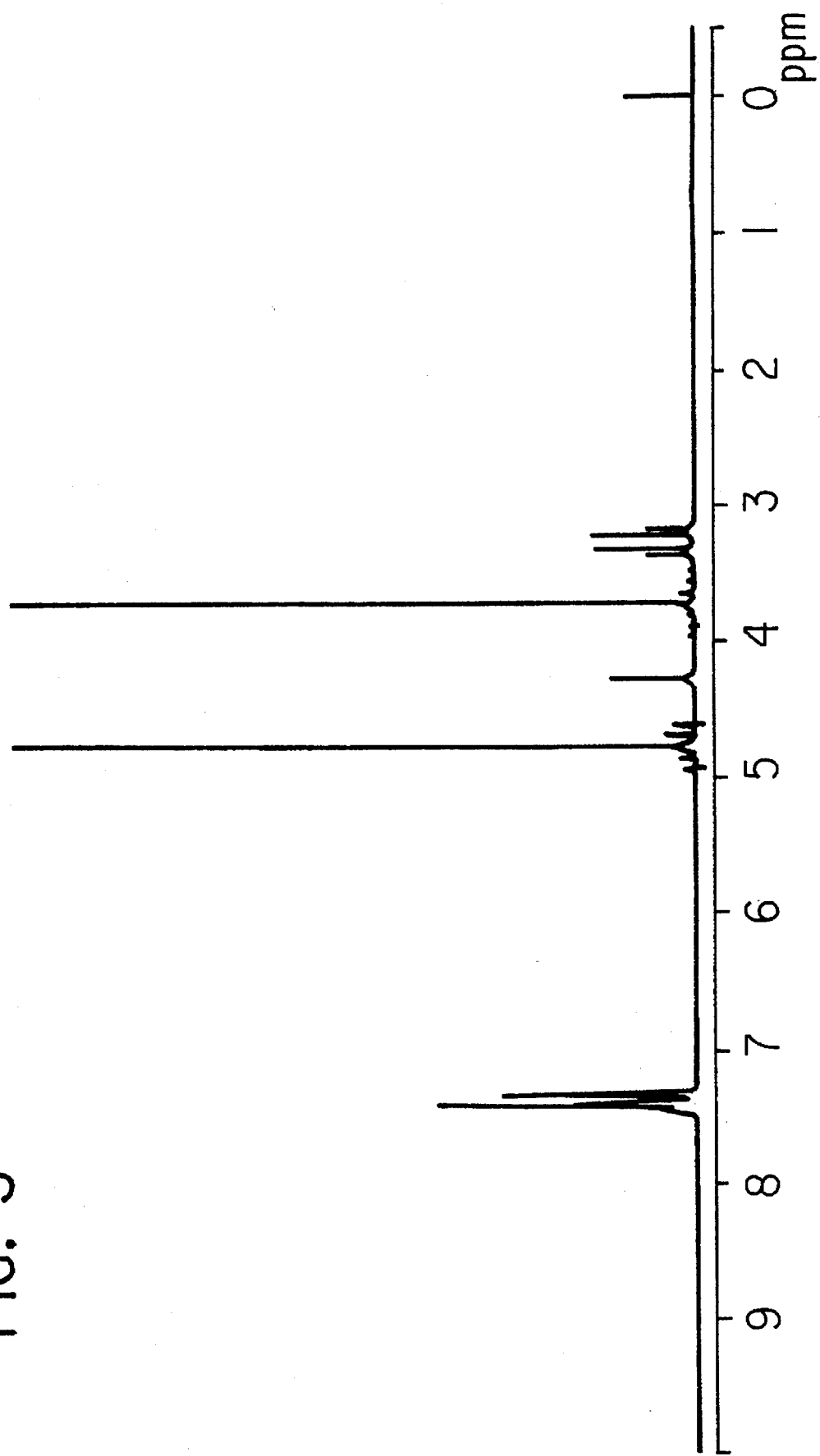
FIG. 3. An NMR chart of a crystal obtained according to Example 1 (solvent; $D_2O$)

Yield, 5.78 g. These crystals were determined as L-Phe.$CH_3SO_4H$ on the basis of various physical property measurements which are summarized in Table 1 and FIGS. 1, 2 and 3.

| | | Calculated Value | Measurement Value |
|---|---|---|---|
| Formation | Carbon | 43.1% | 43.0% |
| | Nitrogen | 5.1% | 5.1% |
| | Sulfur | 11.6% | 11.2% |
| | L-Phe | 59.5% | 60.2% |
| | $Ch_3SO_4H$ | 40.4% | 41.3% |
| | Water | 0.0% | 0.1% |
| Solubility to Solvent | water | | easily soluble |
| | ethanol | | soluble |
| | acetone | | slightly soluble |
| | ether | | slightly soluble |
| Acid-base Condition of Solution | | acidic | |
| Coloration Reaction | | Ruhemann's purple in ninhydrin reaction | |
| Melting Point | | 194.4–195.2° C. (decomposition) | |

*The calculated values of formulation are based on $CH_3SO_4H$.L-Phe

EXAMPLE 2

Example 1 was repeated except that 4.13 g (25 mmol) DL-Phe was used. Yield, 4.57 g. The IR spectrum and the X-ray powder diffraction pattern of the crystals obtained were identical with those of Example 1. In addition, the melting point was 173°–174° C.

EXAMPLE 3

Example 1 was repeated except that 3.72 g (22.5 mmol) L-Phe and 0.41 g (2.5 mmol) D-Phe; (D-Phe/L-Phe=11%) were used. Yield, 5.01 g.

The collected crystals were analyzed by HPLC with an optically active column. The content of D-Phe was only 1% with respect to L-Phe.

Control 1

3.72 g (22.5 mmol) L-Phe and 0.41 g (2.5 mmol) D-Phe (D-Phe/L-Phe=11%) were suspended in 50 ml water, acidified with sulfuric acid and dissolved. The pH of the solution was adjusted to 6 with an aqueous solution of sodium hydroxide and the separated crystals were filtered and isolated at 40° C. Yield, 2.98 g.

The collected crystals were analyzed by HPLC with an optically active column. The content of D-Phe was 14.7% relating to L-Phe.

EXAMPLE 4

6.39 g (0.048 mol) $CH_3SO_4Na$, 1.97 g (11.9 mmol) L-Phe and 98 mg (5 wt. % relating to L-Phe) L-Tyr were suspended in 15 mL of water, and adjusted to pH=0 with sulfuric acid. The mixture was heated and dissolved at 70° C. and cooled. The separated crystals were isolated by suction filtration, washed with a small amount of cold water and dried under reduced pressure. Yield, 2.62 g. These crystals contained 1.54 g (9.3 mmol) L-Phe and 28.6 mg (1.9 wt. % relating to L-Phe) L-Tyr.

Control 2

1.97 g (11.9 mmol) L-Phe and 98 mg (5 wt. % relating to Phe) L-Tyr were suspended in 30 mL of water, heated and dissolved at 80° C. and then cooled slowly to 40° C. The separated crystals were isolated by suction filtration, washed with a small amount of water and dried under reduced pressure. Yield, 0.65 g. These crystals contained 0.59 g (3.6 mmol) L-Phe and 55 mg (9.4 wt. % relating to L-Phe). L-Tyr.

EXAMPLE 5

3.19 g (23.8 mmol) $CH_3SO_4Na$ and 1.97 g (11.9 mmol) L-Phe were added to a mixed solution of 10 ml water and 5 ml acetic acid. The solution obtained was adjusted to pH 0.6 with sulfuric acid and cooled with ice. The separated crystals were isolated by suction filtration. Yield, 1.78 g. The crystals contained L-Phe of 1.01 g.

EXAMPLE 6

A solution of 2.38 g L-Phe.$CH_3SO_4H$ salt dissolved in 9 ml of water was added dropwise to 50 ml of acetone. The mixed solution became turbid. After the crystals were aged in a refrigerator, they were isolated by a suction filtration. Yield after dry, 1.86 g.

EXAMPLE 7

5.8 ml of 95% sulfuric acid was added to 33 ml of methanol and heat-refluxed. Subsequently, methanol was removed under reduced pressure and water was added to provide 15 ml of $CH_3SO_4H$ solution. 2.7 g L-Phe and 0.3 g (D-Phe/L-Phe=11.1%) D-Phe were added thereto and dissolved by heat, following which was then cooled with ice. The separated crystals were isolated by suction filtration and washed with a small amount of cold water. Yield, 3.73 g. The results of HPLC analysis using an optically active column revealed that the crystals contained 1.66 g L-Phe and 0.049 g (D-Phe/L-Phe=2.9%) D-Phe. In addition, 41 mg of L-phenylalanine methyl ester was also produced as a result of esterification of L-Phe with the methanol remaining in the $CH_3SO_4H$ solution.

EXAMPLE 8

500 g (3.03 mol) L-Phe was suspended in 900 mL of methanol, and acidified with 330 g of 98% $H_2SO_4$. The mixed solution was kept at 80° C. while 4,000 ml of methanol was continuously added over 5 hours. Simultaneously, an approximately equal amount of methanol was removed. The reaction solution was neutralized to pH=8.3 with 15% $Na_2CO_3$ solution and the produced L-PM was extracted and isolated with toluene and a water layer of 900 ml was obtained. This water layer contained 7.71 g (46.7 mol) L-Phe and 385 g (2.87 mol) sodium monomethylsulfate.

300 mL of the extracted water layer was adjusted into pH 1 with hydrochloric acid and was concentrated into 100 ml at 60° C. under reduced pressure. The resultant concentrated solution was stirred overnight at 5° C. and the separated crystals were isolated by suction filtration. Yield, 14.52 g. These crystals contained 2.30 g (13.9 mmol L-Phe: yields 89.1%), and 8.20 g (73.2 mol) monomethyl sulfuric acid.

13.2 g of these crystals were dissolved in 30 ml of water and adjusted to pH=5.8 with a solution of sodium carbonate. The solution was stirred and crystallized at 5° C. for two hours. Subsequently, the crystals were isolated by a suction filtration and washed with a small amount of water. The crystals contained 1.36 g (8.2 mmol: yields 64.5%) L-Phe and 0.046 g (0.4 mmol) monomethyl sulfuric acid.

EXAMPLE 9

295 ml of the extracted water layer obtained in Example 8 was concentrated into 100 ml under reduced pressure. The resultant solution was adjusted to pH=2 with hydrochloric acid and cooled to 5° C. The separated crystals were isolated by suction filtration and washed with a small amount of water. Yield, 12.49 g. These crystals contained 1.73 g (10.5 mmol: yields 68.5%) L-Phe.

Control 3

300 ml of the extracted water layer obtained in Example 8 was adjusted to pH=5.6 with hydrochloric acid and concentrated to 100 ml under reduced pressure. The concentrated solution was stirred overnight at 5° C. and the separated crystals were isolated by suction filtration. Yield, 20.7 g. The crystals contained 0.91 g. Yields, 35.5% L-Phe.

EXAMPLE 10

33.75 g (0,204 mol) L-Phe and 3.75 g (22.7 mol) (in total, L-Phe of 36.32 g (0.22 mol) and D-Phe/L-Phe 10.3%) D-Phe were added to 300 ml of the extracted water layer obtained in Example 8. Sulfuric acid was added with heating and when the crystals were completely dissolved, the solution was adjusted to pH=1. The solution was stirred overnight at 8° C. and the separated crystals were isolated by suction filtration. The crystals were washed with a small amount of cold water. Yield, 64.0 g. The crystals contained 32.39 g (0.196 mol: crystallization yields 89.1%) L-Phe, 1.04 g (D-Phe/L-Phe 3.2%) D-Phe and monomethyl sulfuric acid of 27.61 g (0.246 mol).

EXAMPLE 11

The esterified reaction solution where 165.2 g of L-Phe was used as the starting material was obtained in the same manner as Example 8 and the resultant was neutralized with 28% aqueous ammonia. L-PM was extracted with toluene. The water layer after extraction contained L-Phe of 3.04 g. The water layer was adjusted to pH=1 with hydrochloric acid and concentrated into 110 ml under reduced pressure. The concentrated solution was stirred overnight at 5° C. and the separated crystals were isolated by suction filtration. Yields, 15.3 g. The present crystals contained 2.46 g L-Phe. Yields, 80.9% L-Phe.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters patent of the United States is:

1. A method for recovering L-phenylalanine from an aqueous solution containing L-phenylalanine, comprising the steps of:

esterifying L-phenylalanine with methanol in the presence of sulfuric acid to produce a solution of L-phenylalanine methyl ester;

neutralizing said solution of L-phenylalanine methyl ester with a base in the presence of water to form a solution containing L-phenylalanine and L-phenylalanine methyl ester;

extracting said L-phenylalanine methyl ester from said neutralized solution with an organic solvent to form an aqueous solution containing L-phenylalanine;

contacting said aqueous solution containing L-phenylalanine with monomethyl sulfuric acid to form crystals of L-phenylalanine monomethyl sulfate;

separating said crystals from said aqueous solution; and removing monomethyl sulfuric acid from said separated crystals to recover L-phenylalanine.

2. The method of claim 1, wherein said base is ammonia or an inorganic base.

3. The method of claim 1, wherein L-phenylalanine or a mixture of L-phenylalanine and D-phenylalanine is added to said aqueous solution formed by said extracting step.

4. The method of claim 1, wherein said aqueous solution containing L-phenylalanine further comprises an organic solvent selected from the group consisting of methanol, ethanol, acetone, formic acid, acetic acid and acetonitrile.

5. The method of claim 4, wherein the concentration of L-phenylalanine in said aqueous solution containing L-phenylalanine is greater than or equal to 0.1 g/dl.

6. The method of claim 1, wherein the concentration of L-phenylalanine in said aqueous solution of L-phenylalanine is greater than or equal to 1 g/dl.

7. The method of claim 1, wherein the temperature during said contacting step is not higher than 60° C.

8. The method of claim 1, wherein the amount of monomethyl sulfuric acid is equimolar to 100 times the corresponding amount of L-phenylalanine in said contacting step.

* * * * *